United States Patent [19]

Gazzi et al.

[11] Patent Number: 4,529,424
[45] Date of Patent: Jul. 16, 1985

[54] CRYOGENIC PROCESS FOR FRACTIONALLY REMOVING ACIDIC GASES FROM GAS MIXTURES

[75] Inventors: Luigi Gazzi, Milan; Giancarlo Cotone, S. Donato Milanese; Gianfranco Soldati, S. Donato Milanese; Alessandro Ginnasi, S. Donato Milanese; Alessandro Vetere, Milan; Carlo Rescalli, S. Donato Milanese, all of Italy

[73] Assignee: Snamprogetti, S.p.A., Milan, Italy

[21] Appl. No.: 393,309

[22] Filed: Jun. 29, 1982

[30] Foreign Application Priority Data

Jul. 23, 1981 [IT] Italy ................................ 23082 A/81

[51] Int. Cl.³ ........................... F25J 3/00; F25J 3/02
[52] U.S. Cl. .......................................... 62/17; 55/68; 55/73
[58] Field of Search .................. 62/17, 20; 203/42; 55/68, 73; 208/332-334

[56] References Cited

U.S. PATENT DOCUMENTS

| | | | |
|---|---|---|---|
| 1,732,371 | 10/1929 | Luther et al. | 208/329 |
| 2,045,321 | 6/1936 | Clarke | 208/329 |
| 4,302,220 | 11/1981 | Volkamer et al. | 55/73 |

Primary Examiner—Frank Sever
Attorney, Agent, or Firm—Morgan, Finnegan, Pine, Foley & Lee

[57] ABSTRACT

A process is described for stripping acidic gases, mainly hydrogen sulphide and carbon dioxide, from natural gas or synthesis gas, especially when the percentages of such acidic gases are high and the conventional processes become economically objectionable.

The process is based on the use of a number of selective solvents, generally belonging to the class of esters, ethers, mixed ester-ethers and lactones, in combination with sequential absorbing cycles which start from the stripping of hydrogen sulphide, and comprise the regeneration of the solvents used by several expansion cycles: H₂S and CO₂ are recovered and the regenerated solvents recycled.

20 Claims, 1 Drawing Figure

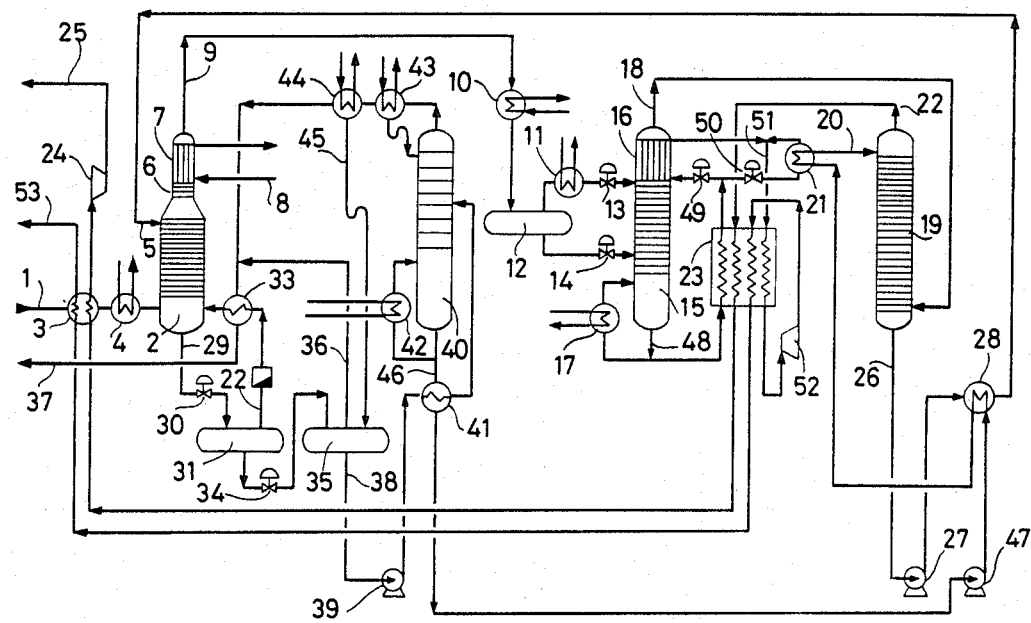

CRYOGENIC PROCESS FOR FRACTIONALLY REMOVING ACIDIC GASES FROM GAS MIXTURES

This invention relates to a process for the removal of acidic gases such as hydrogen sulphide and carbon dioxide from gas mixtures containing them, said process being particularly suitable for treating gaseous mixtures which have acidic gas contents of an even very high magnitude.

The processes of the conventional art for solving such a problem are technologically indicated to treat gases which, in the raw condition, contains comparatively slight percentages of acidic gases.

These conventional processes, in fact, have been influenced by the circumstance that they had been devised in times when the cost of power was relatively low so that only natural gases having low percentages of the acidic components aforesaid were exploited.

Such processes of the conventional technology can, of course, be exploited also for treating gases having a high content of acidic components, but the results, both from the economical and the technical viewpoint, can become unacceptable under stringest conditions.

As a matter of fact, these processes are essentially based on the absorption with selective solvents which retain the acidic components and leave the purified gas free.

The cost of the treatment, thus, is, with a fair approximation, proportional to the quantity of solvent which is employed with respect to the volume of gas to be handled. Such quantity of solvent is a growing function of the contents of acidic components. The cost of the treatment must thus be attributed to the purified gas.

It becomes thus apparent that the treatments according to the conventional technology have costs which grow unacceptably as the contents of the acidic gases grows.

Under the present conditions of power shortage, the best course is to exploit the available resources to their best.

To start production in gas fields in which gases with a high contents of acidic components are found, or to purify synthesis gases produced from fuel oil or coal, the necessity is strongly felt for handling processes which are suitable for gases having high and very high contents of acidic components and which can fulfil even very rigorous specifications.

The treatment of gases of the kind referred to above requires the adoption of mixed technologies, that is with cryogenic means and with a solvent so as to combine the advantages of the two routes and to obtain thereby a satisfactory purification of the gases concerned at acceptable costs.

The present Applicants have already claimed a process of the kind referred to above by their British Pat. No. 1 555 068 filed Mar. 3, 1977. The Patent in question discloses the purification of a raw gas which contained more than 70% of acidic gases by the combined use of a low-temperature distillation step and an absorption step using a solvent. The solvents described in the Patent are dimethyletherpolyglycol and propylene carbonate.

A novel purification process has now been found, which is particularly adapted to treat gases having a high percentage of acidic gases and which exploits a class of selective solvents which are particularly suitable for the purification by a cryogenic cycle.

An object of the present invention is to employ such solvents in the treatment cycle to be described hereinafter.

The solvents to be used in the process according to this invention are, above all, esters and ethers having a low molecular weight and belonging to the following classes:

esters of alcohols of the general formula $R_1COOR_2$ wherein $R_1$ and $R_2$ are alkyls having from 1 to 4 carbon atoms, equal to or different from one another, such as methyl formate, methyl acetate and ethyl acetate;

esters of glycols of the general formula:

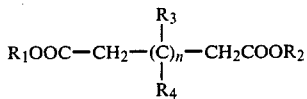

wherein $R_1$ and $R_2$ are alkyls having from 1 to 3 carbon atoms, equal to or different from one another, $R_3$ and $R_4$ equal to or different from one another, are either alkyls having from 1 to 3 carbon atoms, or hydrogen atoms, n is an integer which can be either 0 or 1, such as 1,3-propanediol acetate, and 2,2-dimethylpropanediol diacetate.

cyclic esters (lactones) of the formula:

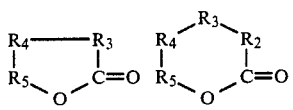

wherein $R_2$, $R_3$, $R_4$, $R_5$, equal to, or different from each other, are alkylenes of which the hydrogen can optionally be substituted by alkyls or methoxy groups:

Open-chain or cyclic ethers such as

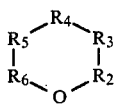

wherein $R_2$, $R_5$, $R_6$, equal to, or different from each other, are alkylenes in which the hydrogen can optionally be substituted by alkylene or methoxy groups, $R_3$ can be an oxygen atom or an alkylene group in which the hydrogen can optionally be substituted by alkyl or methoxy groups, $R_4$ can be the same as $R_5$ or be absent in the case of a 5-membered ring, such as tetrahydrofuran, methyltetrahydrofuran, tetrahydropyran, 1,3-dioxolan;

diethers having the general formula:

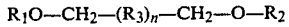

wherein $R_1$ is an alkyl having from 1 to 4 carbon atoms, $R_2$ is hydrogen or an alkyl of from 1 to 4 carbon atoms, or a hydrogen atom, $R_3$ is either an alkylene or a ($CH_2$—O—$CH_2$) group, n being an integer which can be either 0 or 1, such as 1,2-dimethoxyethane, 1,2-methoxyethoxyethane, dimethoxydiethyleneglycol, 1-methoxyethanol;

monoethers having the general formula $R_1$—O—$R_2$, wherein $R_1$ and $R_2$, equal to or different from one another, are alkyls having from 1 to 4 carbon atoms;

esters-ethers, that is compounds containing both the esteric and the etheric functions, having the general formula:

$$(R_4-O-)_n-R_1-COOR_2-OR_3$$

wherein $R_3$ and $R_4$, equal or different from one another, are alkyls having from 1 to 4 carbon atoms, $R_2$ is an alkylene group having from 1 to 4 carbon atoms, $R_1$ is the same as $R_2$ or the same as $R_3$, n is an integer which can be either 0 or 1, such as 2-methoxyethyl acetate.

The solvents referred to above combine a number of properties which are quite favourable to their use as selective solvents.

As a matter of fact, they have a high stability under the conditions of use, they have a high solvent power relative to the acidic gases, they possess a high selectivity towards $H_2S$ relative to $CO_2$ and the hydrocarbons in general, a high selectivity for $CO_2$ with respect to the hydrocarbons, and, in addition, they have a low molecular weight and a low melting point. The latter characteristic is vital for their use in a cryogenic process.

In the case when a natural gas is being treated, after the low-temperature distillation and prior to the final purification with a solvent, the gas is available at very low temperatures, considerably lower than zero centigrade.

During progress of the final purification, it is an advantage to be able to attain temperatures which are considerably lower than the temperature of the gas, that which is an asset because the absorbing power of the solvent is thereby increased and its selectivity as well.

The solvents for the process according to this invention have a low melting point and are thus quite particularly suitable for being used in a cryogenic process.

The solvents referred to above, in addition, have the property of being markedly selective towards hydrogen sulphide as compared with carbon dioxide so that they provide a good measure of safety relatively to the most hazardous component.

The solvents according to the invention can be used alone, or in admixture with each other, or they can be admixed with water and/or with an organic compound having a low melting point, such as dimethyl ether, methanol, acetone with a view to adjust the solvent power as a function of the gases to be treated and the conditions of the gas to temperature and pressure.

The process according to the invention, inter alia, permits to obtain substantially separate vent streams containing $CO_2$ and $H_2S$, respectively, comprises the following steps:

(a) Feeding the natural gas or the synthesis gas to a first absorption column to absorb $H_2S$, by one or more solvents selected from among those mentioned hereinabove;

(b) Feeding the substantially $H_2S$-stripped gas to a low-temperature distillation column having the task of reducing the carbon dioxide contents, from the bottom of said column liquefied carbon dioxide being substantially drawn;

(c) Feeding the gas emerging from the low-temperature distillation column to a second absorption column to reduce the contents of carbon dioxide to the desired value, by one or more solvents selected from among those mentioned hereinabove;

(d) Regenerating the solvent(s) used for the absorption of $H_2S$ and $CO_2$ initially by one or more expansion stages wherefrom the useful components absorbed together in the stages (a) and (c) are recovered, to be recycled to the first absorption column, then by another or a number of additional expansion stages wherefrom $CO_2$ and $H_2S$ are recovered and subsequently by means of a second distillation column from the head of which $H_2S$ and $CO_2$ emerge, and (e) Recycling the regenerated solvent(s) first to the absorption column of (c) and then subsequently in series to the first absorption column of stage (a).

The first absorption column, that is the desulphurizing stage (a) works under a pressure comprised between 35 and 80 abs. atmospheres, whereas the temperature can be selected between $-30°$ C. and $+20°$ C.

The low-temperature distillation column, stage (b) works under a pressure comprised between 30 and 75 abs. atm. preferably between 35 and 55 abs.atm. whereas the head temperature must be selected between $-57°$ C. and $-30°$ C. and the bottom temperature between $-7°$ C. and $+31°$ C.

The second absorption column, stage (c), works under the same pressure (pressure drops excepted) as the distillation column, that is, between 30 and 75 abs.atm. whereas the temperature must be selected between $-100°$ C. and $-10°$ C.

The second distillation column, regeneration stage (d), works under a pressure comprised between 1.1 and 3 abs.atm. whereas the head temperature can be selected from $30°$ C. to $50°$ C. and the bottom temperature between $55°$ C. and $100°$ C.

The expansion stages of stage (d) can be from 2 to 6 in total, the last stage working under a pressure of from 0.2 to 2 abs.atm.

The invention will now be more clearly described with the aid of the diagram of the accompanying single FIGURE of the drawings which shows a preferred embodiment which, however, must not be taken as a limitation of the invention.

The synthesis gas as obtained from fuel oils or coal, and composed of variable percentages of $H_2$, $N_2$, CO, methane, from 30% to 60% of $CO_2$ and from a few tenths to a few percentage units of $H_2S$, which is available at ambient temperature and under pressures variable, according to the individual situations, from 35 to 80 abs/atm. is fed via the pipeline 1 to the absorption column 2, after having previously been pre-cooled with process streams and, optionally, with an external refrigerating fluid in the exchangers 3 and 4 down to a temperature which is slightly above the dew point of the gas concerned.

In the absorption column 2, the raw gas is scrubbed in countercurrent relationship with one of the solvents referred to above which enter through the pipeline 5 to strip it of $H_2S$ until a concentration of $H_2S$ below 1 part per million (ppm) is achieved.

Optionally, the solvent entrained by the gas stream is recovered by a rectification trunk 6, the dephlegmator 7 of which is cooled with an external cooling fluid 8.

The gas 9, exiting the column top, stripped from $H_2S$, is cooled and optionally split into two (or more) fractions by fractional condensation by means of the cooling units 10 and 11 and the separator 12; the two fractions are fed via the valves 13 and 14 to the low-temperature distillation column 15, which has a dephlegmator 16 and a reboiler 17; the latter is heated by condensing a portion of a refrigerating fluid. The column 15 has the task of reducing the $CO_2$ contents.

If there is a pressure differential of at least 3 atm. between the $H_2S$-stripped gas and the working pressure of the column 15, the gas or the portion thereof which is left in the vapour state after pre-cooling or fractional condensation can be expanded in a turbine so as to produce both refrigeration and power. The gas exiting the top 18, of the distillation column and which still contains $CO_2$ (from 20% to 30% molar) is sent to a second absorption column 19 so as further to reduce, even to a few tenths of ppm. the contents of carbon dioxide by a countercurrent scrubbing with the selected solvent.

The solvent, prior to being sent to the column 19 through the pipeline 20 is cooled with processing streams by vaporization of $CO_2$ in the exchanger 21 at a temperature ranging from $-20°$ C. to $-57°$ C.

The purified gas 22 emerging from the top of the second absorption column is heated in the exchangers 23 and 3 to recover its negative calories and is compressed to the pressure of use in the compressor 24 before leaving the installation via the pipeline 25.

From the bottom of the second absorption column 19 the solvent 26 enriched with $CO_2$ is drawn and sent via the pump 27 to the first absorption column via 5 after having been heated in the exchanger 28.

From the bottom of the first absorption column 2, one obtains a stream 29 which contains $H_2S$, $CO_2$, the solvent which has been used and a small fraction of the useful compounds contained in the raw gas.

To regenerate the solvent contained in it, the stream is expanded in more expansion stages (two in the example shown) and then distilled in a specially provided column.

The stream 29, after having been expanded through the valve 30 is separated in the separator 31 to produce a gaseous phase which contains useful components and which is compressed at 32 and recycled to the first absorption column after having been cooled in the exchanger 33, and a stream which undergoes a second expansion through a valve 34 to be separated, in its turn, in the separator 35, into a gaseous phase 36 which obtains the major fraction of $H_2S$ which is heated in the exchanger 33 and which leaves the installation via the pipeline 37, and a stream which contains the major fraction of the solvent 38 (now partially regenerated) which, via the pump 39 is fed to the regeneration column 40 after having been heated in the exchanger 41.

The regeneration column works under pressure from 1.1 to 3 abs.atm. at a head temperature between 30° C. and 50° C. and at a bottom temperature from 55° C. to 100° C.

From the latter column head a gas exits which contains $H_2S$ and $CO_2$, which is cooled at 44 by an external cooling fluid. To recover the evaporated solvent which shall be recycled at 35 through the pipeline 45 to be finally admixed with the $H_2S$-rich stream 36 emerging from the second separator.

The regenerated solvent emerging from the bottom 46 of the regeneration column 40 is cooled at 41 and sent via the pump 47 to the second absorber 19 after having been cooled at 28 again.

From the bottom of the distillation column 15 a stream is drawn which essentially contains liquefied $CO_2$, 48, which is undercooled in the exchanger 23 and optionally split into two streams, either of which expanded through the valve 49 and vaporized in the dephlegmator 16, the other being expanded through the valve 50 and vaporized in the exchanger 21 to cool the regenerated solvent, prior to being recycled to the column 19. If the stream which contains liquefied $CO_2$ is not split, the whole stream is expanded in valve 49 and vaporized in the dephlegmator 16.

The expansion in the two valves takes place under a pressure comprised between 5.3 and 8 abs.atm.

The two vaporized streams are combined into a single stream 51, which is heated at 23, expanded in the turbine 52 under a pressure which is about the atmospheric pressure and heated at 23 again and finally sent to be dispersed into the atmosphere via the pipeline 53.

The turbine 52 can possibly be replaced by a valve.

Optionally, the gas emerging through the top of the distillation column, before being sent to the second absorption column, can be combined with a portion of the exhausted solvent taken from the last plate of the second absorption column: the mixture so formed is cooled in an exchanger by a fraction of the liquid $CO_2$ stream as produced by the low-temperature distillation column and sent to a separator (this can be placed at the bottom of the second absorption column, if desired) wherefrom the solvent to be regenerated is obtained along with the partially purified gas which is fed under the last plate of the second absorption column.

The flowing volume of solvent which is necessary for removing the $CO_2$ which has been left after low-temperature distillation is about the same as is required for removing $H_2S$, so that the same quantity of solvent flows through the two absorbers 19 and 2 serially.

If the solvent rate of flow which is required to remove $H_2S$ is greater, a portion of the solvent pumped at 47 should skip the column 19 to enter the absorber 2 directly.

If the quantity of solvent required for the final purification of $CO_2$ is greater, a portion of the solvent exiting the absorber 19 should be regenerated by sequential expansions and pumped to the absorber 19 again.

We claim:

1. A cryogenic process for the fractional removal of acidic gases, such as $H_2S$ and $CO_2$ from natural gas or syngas comprising the steps of:
    (a) feeding the natural gas or syngas in countercurrent relationship with a solvent for selective absorption of acidic gases, the solvent being selected from a group comprising methyl formate, methyl acetate, ethyl acetate, tetrahydropyran, 1,3-dioxolane, tetrahydrofuran, methyltetrahydrofuran, 1,2-dimethoxyethane, 1,2-methoxyethoxyethane, 1-methoxyethanol and 2-methoxyethyl acetate, and mixtures thereof, under a pressure of between 35 to 80 absolute atmospheres and at a temperature in the range of $-30°$ C. to $+20°$ C.;
    (b) feeding the gas substantially stripped of $H_2S$ to a distillation column under a pressure of between 30 to 75 absolute atmospheres, at a head temperature of from $-57°$ C. to $-30°$ C. and a bottom temperature from $-7°$ C. to $+30°$ C. to remove $CO_2$ in the form of a liquid;
    (c) feeding the gas from the distillation column to a second absorption column in countercurrent relationship to said solvents for selective absorption under the same pressure as the distillation column and at a temperature in the range of between $-100°$ C. to $-10°$ C. to further remove the $CO_2$;
    (d) regenerating the spent solvents from the first and second absorption columns by one or more expansion stages to recover the solvents which are recycled to the first absorption column;
    (e) stripping the $CO_2$ and $H_2S$ from the spent solvents by additional expansion stages;

(f) feeding the solvent recovered in step (e) to a second distillation column, to further remove $H_2S$ and $CO_2$, under a pressure between 1.1 to 3 absolute atmospheres at a head temperature in the range of 30° C. to 50° C. and a bottom temperature in the range of between 55° C. to 100° C.; and (g) recycling the regenerated solvents from steps (e) and (f) to the second absorption column.

2. A process according to claim 1, wherein the pressure is comprised between 35 and 55 abs. atm.

3. A process according to claim 1, wherein the expansion stages of step (d) can be in total from 2 to 6.

4. A process according to either of claims 1 or 3, characterized in that the last expansion stage of step (d) works under a pressure comprised between 0.2 and 2 abs.atm.

5. A process according to claim 1, characterized in that a rectification section fitted with a dephlegmator is inserted serially with the first absorption column of stage (a).

6. A process according to claim 1, characterized in that the gas which has been substantially stripped of $H_2S$ prior to being sent to the low-temperature distillation column of stage (b) is split into two or more fractions by fractional condensation.

7. A process according to claim 1, characterized in that the gas which has been substantially stripped of $H_2S$ or the portion thereof which is still in the vapour state after pre-cooling or fractional condensation can be expanded in a turbine prior to being fed to the low-temperature distillation column.

8. A process according to claim 1, characterized in that the liquefied carbon dioxide drawn from the bottom of the low-temperature distillation column of stage (b) is undercooled in an exchanger, expanded and vaporized totally or partially in the condenser of the distillation column and the possible remaining part in an exchanger the resultant $CO_2$ stream(s) being heated in the same exchanger as the liquid $CO_2$, subsequently and further expanded by turbine or valve and finally heated again in the same exchanger as the liquid $CO_2$.

9. A process according to claims 1 or 8, characterized in that the pressure at which the $CO_2$ is expanded immediately after having been cooled is comprised between 5.3 and 8 abs.atm. and that the pressure at which the $CO_2$ is expanded immediately after having been vaporized and heated is about the atmospheric pressure.

10. A process according to claim 1, characterized in that a portion of the regenerated solvent is recycled directly to the first absorption column, the second absorption column being omitted.

11. A process according to claim 1, characterized in that a part of the solvent exiting the second absorption column is regenerated by subsequent expansion and recycled to the second absorption column.

12. A process according to claim 1, characterized in that part of the exhausted solvent drawn from the last plate of the second absorption column of stage (c) is combined with the gas coming from the low-temperature distillation column of stage (b) and that the mixture thus formed is cooled in an exchanger with a portion of the liquid $CO_2$ stream produced in the low-temperature distillation column and is sent to a separator in which the solvent to be regenerated is obtained together with the partially purified gas which is fed to the absorption column.

13. A process according to claim 1, wherein water and/or an organic compound having a low melting point is added to the selective solvent.

14. A process according to claim 13 wherein the organic compound having a low melting point is added in a proportion comprised between 0.3% and 40% of the resultant mixture.

15. A process according to claim 13 or 14 wherein the organic compound is methanol or dimethylether or acetone.

16. A process according to claim 1, wherein the solvent for selective absorption is selected from a group consisting of methyl formate, methyl and ethyl acetate, and mixtures thereof.

17. A process according to claim 1, wherein the solvent for selective absorption is selected from a group consisting of tetrahydropyran, 1,3-dioxolane, tetrahydropuran and methyltetrahydrofuran, and mixtures thereof.

18. A process according to claim 1, wherein the solvent for selective absorption is selected from a group consisting of diacetate of 1,3-propanediol and the diacetate of 2,2-dimethyl-1,3-propanediol, and mixtures thereof.

19. A process according to claim 1, wherein the solvent for selective absorption is selected from a group consisting of 1,2-dimethoxyethane, 1,2-methoxyethoxyethane, dimethoxydiethyleneglycol and 1-methoxyethanol.

20. A process according to claim 1, wherein the solvent for selective absorption is 2-methoxyethylacetate.

* * * * *